United States Patent [19]
McCarthy et al.

[11] Patent Number: 5,512,678
[45] Date of Patent: Apr. 30, 1996

[54] 5-(1-FLUORO-VINYL)-1H-PYRIMIDINE-2,4-DIONE DERIVATIVES USEFUL AS ANTINEOPLASTIC AGENTS

[75] Inventors: James R. McCarthy, Solona Beach, Calif.; Donald P. Matthews, West Chester; Jeffrey S. Sabol, Loveland, both of Ohio

[73] Assignee: Merrell Pharmaceuticals Inc., Cincinnati, Ohio

[21] Appl. No.: 236,599

[22] Filed: Apr. 29, 1994

Related U.S. Application Data

[63] Continuation-in-part of Ser. No. 121,405, Sep. 14, 1993, abandoned.

[51] Int. Cl.$^6$ .................... C07D 405/04; C07D 239/02; A61K 31/505
[52] U.S. Cl. .................... 544/310; 544/313; 544/314
[58] Field of Search .................... 544/310, 313, 544/314; 514/269

[56] References Cited

U.S. PATENT DOCUMENTS

| | | | |
|---|---|---|---|
| 4,425,573 | 11/1983 | Ochi et al. | 544/311 |
| 4,864,021 | 9/1989 | Fujii | 536/23 |

OTHER PUBLICATIONS

Tetrahedron Letters, vol. 35, No. 29, 18 Jul. 1994, Oxford GB pp. 5177–5180, Matthews D. P. et al. "The Synthesis of (1–Fuorovinyl) Tributyltin: A Synthetic Equivalent for the 1–Fluoroethene Anion", see p. 5177; Table 1.
Bobek, et al., J. Med. Chem. 30(8):1498–97 (1987).
Coe, et al., J. Med. Chem. 25(11):1329–34 (1982).
Walker, et al., Nucleic Acids Symp. Ser., 11 (Symp. Nucleic Acids Chem., 10th, 1982) 215–218 (1982).
Baerwolf, et al., Nucleic Acids Symp. Ser. 9:45–47 (1981).
Kumar, et al., Eur. J. Med. Chem. 26(5):557–562 (1991).
Farrina, et al., Synlett (3):157–159 (1991).
Coe, et al., CA 97 (19): 163396A (1982).
Walker, et al, CA 98 (11): 83248j (1982).
Balzarini, et al., CA 98 (7): 46574s (1982).
Walker, et al., CA 97 (9): 72715n (1982).
Balzarini, et al., CA 98 (25): 209571e (1982).
Barr, et al., CA 95 (11): 98197d (1981).
Spector, et al., CA 116 (21): 207803y (1992).
Balzarini, et al., CA 108 (17): 142949 (1987).
Balzarini, et al., CA100 (25): 202993V (1984).
Jones, et al., CA96 (25): 218192y (1981).
De Clercq et al., CA 94 (23): 185443d (1981).
Barr, et al., CA 86 (11): 72565m (1976).
Baerwolff, et al., CA 85 (7): 46986j (1975).
De Clercq et al., CA 91(17): 133836c (1979).
Barwolff, D., et al., CA 87, (48) 335428 (1979).
De Clercq, et al., Proc. Natl. Acad. Sci., vol. 76, 6:2947–2951 (1979).
Bleackley, et al., Tetrahedron, 32:2795–2797 (1976).
Baerwolff, et al., CA 109:6907s, p. 660 (1988).
Matthews, D. P. et al., Tetrahedron Letters, vol. 35, No. 7 pp. 1027–1030. (1994).
Balzarine, J. et al, Biochem. Pharmacol., 31(22), 3673–3682 (1982).
Balzarine et al., Proc. Int. Round Tabel Nucleosides, Nucloetides Their Biool. Appl., 4th, Meeting date 1981, 275–291 (1982).
DeClercq etl al., Mol Pharmacol., 19(2), 321–330 (1981).
Baerwolff, D. et al., Nucleic Acids Res. Spec. Publ., 1(Symp. Chem. Nucleic Acids Components, 3rd, 1975), 529–531, (1975).
John A. Wilkinso, Chemical Reviews, 92, 505 (1992).

*Primary Examiner*—Cecilia Tsang
*Attorney, Agent, or Firm*—Nelson L. Lentz

[57] ABSTRACT

The present invention provides novel 5-(1-fluorovinyl)-1H-pyrimidine-2,4-dione derivatives which are useful as antineoplastic agents by themselves or in conjunctive therapy with the antineoplastic agent 5-fluorouracil.

8 Claims, No Drawings

5-(1-FLUORO-VINYL)-1H-PYRIMIDINE-2,4-DIONE DERIVATIVES USEFUL AS ANTINEOPLASTIC AGENTS

This application is a continuation-in-part of application Ser. No. 08/121,405, filed Sep. 14, 1993, abandoned.

FIELD OF THE INVENTION

The present invention relates to novel 5-(1-fluorovinyl)-1H-pyrimidine-2,4-dione derivatives which are useful as antineoplastic agents by themselves and in conjunctive therapy with the antineoplastic agent 5-fluorouracil.

BACKGROUND OF THE INVENTION

Neoplastic disease states in humans are recognized throughout the world as being serious and oftentimes life-threatening conditions. These neoplastic diseases, which are characterized by rapidly-proliferating cell growth, have been and continue to be the subject of worldwide research efforts directed toward the identification of therapeutic agents which are effective in the treatment of patients suffering therefrom. Effective therapeutic agents can be characterized as those which prolong the survivability of the patient, which inhibit the rapidly-proliferating cell growth associated with the neoplasm, or which effect a regression of the neoplasm. Research in this area is primarily focused toward identifying agents which would be therapeutically effective in humans. Typically, compounds are tested for antineoplastic activity in small mammals, such as mice, in experiments designed to be predictive of antineoplastic activity not only in those animals but also in humans against specific neoplastic disease states.

SUMMARY OF THE INVENTION

The present invention provides novel 5-(1-fluorovinyl)-1H-pyrimidine-2,4-dione derivatives having the following general formula I:

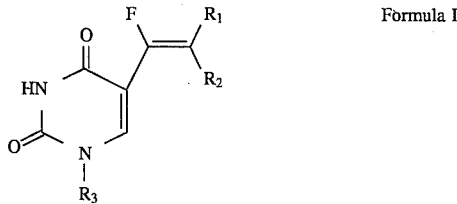

Formula I wherein $R_1$ and $R_2$ are each independently hydrogen, $C_1$–$C_4$ alkyl, or a phenyl group unsubstituted or substituted with from 1 to 3 substituents, wherein each substituent is selected from the group consisting of $C_1$–$C_4$ alkyl and $C_1$–$C_4$ alkoxy; and $R_3$ is hydrogen, ribose, 2'-deoxyribose or arabinose.

The present invention provides a method of treating a patient suffering from a neoplastic disease state comprising administering to said patient an effective antineoplastic amount of a compound of formula (I).

In addition the present invention provides a method of treating a patient suffering from a neoplastic disease state comprising administering to said patient an effective antineoplastic amount of a compound of formula (I) in conjunctive therapy with an effective antineoplastic amount of 5-fluorouracil.

The present invention further provides a method of inhibiting thymidylate synthetase in a patient in need thereof comprising administering to said patient an effective inhibitory amount of a compound of formula (I).

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl, and the like. The term "$C_1$–$C_4$ alkoxy" refers an alkyloxy radical made up of an oxygen radical bearing an saturated straight or branched chain hydrocarbon radical of one to four carbon atoms. Included within the scope of this term are methoxy, ethoxy, propyloxy, isopropyloxy, n-butyloxy, isobutyloxy, sec-butyloxy, t-butyloxy and the like. The term "halogen" or "halo" refers to a chlorine, bromine or iodine atom. The substituents described for the substituted phenyl group may be the same or different and may be located at any of the ortho, meta, or para positions. The term "Pg" refers to a suitable protecting group.

The term "stereoisomer" refers to a compound made up of the same atoms bonded by the same bonds but having different three-dimensional structures which are not interchangeable. The three dimensional structures are called configurations. The term "enantiomer" refers to two stereoisomers whose molecules are nonsuperimposable mirror images of one another. The term "racemic mixture" or "racemic modification" refers to a mixture of equal parts of enantiomers. The term "chiral center" refers to a carbon atom to which four different groups are attached.

It is understood that these compounds of formula (I) may exist in a variety of stereoisomeric configurations. It is further understood that the maximum number of enantiomers possible for each compound is equal to $2^n$ wherein n represents the total number of chiral centers located on the compound. These stereoisomers, including the enantiomers are specifically understood to be included within the scope of the present invention.

Starting material for preparation of compounds of formula (I) can be prepared as described in Schemes I and II. All substituents, unless otherwise indicated, are previously defined. The reagents and starting materials are readily available to one of ordinary skill in the art.

Scheme I

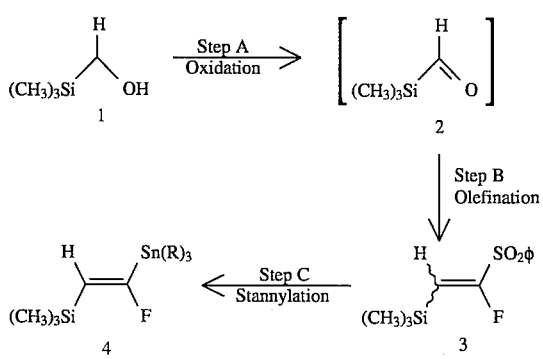

R = $C_1$–$C_4$ alkyl or phenyl
φ = phenyl

In Scheme I, step A the trimethylsilylmethanol of structure (1) is oxidized to provide the aldehyde of structure (2) under conditions well known in the art. [See Ireland, R. E. and Norbeck, D. W., *J. Org. Chem.*, 50, 2198 (1985)] For example 1.4 equivalents of oxalyl chloride is dissolved in a suitable organic solvent, such as dichloromethane and the solution is cooled to about −78° C. To this is added 1.6 equivalents of dimethyl sulfoxide dissolved in dichloromethane over about 20 minutes. After addition is complete the reaction is stirred for an additional 10 minutes and an equivalent of trimethylsilylmethanol is added. The reaction is stirred for an additional 15 minutes at −78° C. and 3.5 equivalents of triethylamine are added. The reaction is stirred for about 20 minutes at −78° C. to produce the aldehyde (2).

In Scheme I, step B the aldehyde (2) is subjected to an olefination reaction to produce the vinyl sulfone described by structure (3). For example, approximately one equivalent of fluoromethylphenyl sulfone [prepared as described by McCarthy, J. R. et al. *Tetrahedron Lett.*, 31, 5449, (1990)] is dissolved in a suitable anhydrous organic solvent, such as tetrahydrofuran under an inert atmosphere, such as nitrogen. The solution is cooled to about −78° C. and 2 equivalents of a suitable base are added. Examples of suitable bases are lithium diisopropylamide (LDA), lithium hexamethyldisilylamide (LiHMDS) and the like. The preferred suitable base is lithium diisopropylamide. This is followed by addition of one equivalent of diethyl chlorophosphate. The reaction is stirred for about 1 to 3 hours at about −78° C. This solution is then added via cannula to the above prepared aldehyde (2) which is already in solution at about −78° C. The reaction is stirred at about −78° C. for 1 to 2 hours and then quenched with saturated ammonium chloride. The product is isolated and purified by techniques well known in the art. For example, the reaction is extracted with a suitable organic solvent, such as ethyl acetate. The combined organic extracts are dried over anhydrous magnesium sulfate, filtered and concentrated under vacuum. The residue is purified by flash chromatography using silica gel and a suitable eluent, such as ethyl acetate/hexane to provide the vinyl sulfone (3).

In Scheme I, step C the vinyl sulfone (3) is subjected to a stannylation reaction to produce the (fluorovinyl)stannane derivative of structure (4). For example the above prepared vinyl sulfone (3), under an inert atmosphere, such as nitrogen, is dissolved in a suitable solvent. Examples of suitable solvents are toluene, benzene, cyclohexane and the like. The preferred suitable solvent is toluene. At least 2 equivalents of a suitable stannylating reagent of formula $(R)_3SnH$ are then added. Examples of suitable stannylating reagents are tributyltin hydride, triethyltin hydride, trimethyltin hydride, triphenyltin hydride and the like. The preferred stannylating reagent is tributyltin hydride. The reaction is initiated by employing a suitable initiator. Suitable initiators are azoisobutyronitrile (AIBN), UV light, triethylboron and the like. The preferred suitable initiator is AIBN. About 0.05 to 0.3 equivalents of AIBN is added and the reaction is heated at reflux for 12 to 48 hours. Additional amounts of AIBN may be added in portions of about 0.05 to 0.3 equivalents of AIBN during reflux as determined by one skilled in the art until all the starting material is consumed. After cooling the product is purified by techniques well known in the art such as flash chromatography utilizing silica gel and a suitable eluent, such as hexane to provide the (fluorovinyl)stannane (4).

Scheme II

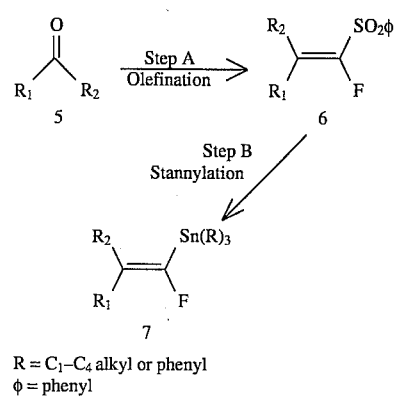

$R = C_1-C_4$ alkyl or phenyl
$\phi$ = phenyl

In Scheme II, step A a ketone or aldehyde of structure (5) is subjected to an olefination reaction to provide the vinyl-sulfone described by structure (6). For example, fluoromethylphenyl sulfone is dissolved in a suitable organic solvent, such as tetrahydrofuran and cooled to about −78° C. About 1.04 equivalents of diethyl chlorophosphate is added followed by addition of about 1.3 equivalents of a suitable base, such as lithium hexamethyldisilamide. After about one hour of stirring at about −78° C. an excess of a suitable ketone or aldehyde is added. Examples of suitable ketones and aldehydes are acetone, acetaldehyde, propionaldehyde, butyraldehyde, valeraldehyde, 2-propanone, 2-butanone, 2-hexanone, 3-hexanone, 3-heptanone, 4-heptanone, benzaldehyde, anisaldehyde, acetophenone, 4-methoxyacetophenone, 4-cyanobenzaldehyde, p-tolualdehyde, hydrocinnamaldehyde and the like. The reaction is then allowed to warm to room temperature and is quenched by addition of saturated ammonium chloride. The product is then isolated and purified by techniques well known in the art. For example, the organic solvent is removed under vacuum and the aqueous is extracted with a suitable organic solvent, such as methylene chloride. The combined organic extracts are dried over anhydrous magnesium sulfate, filtered and concentrated under vacuum. The residue is purified by flash chromatography using silica gel and a suitable eluent, such as ethyl acetate/hexane to provide the vinyl sulfone (6).

In Scheme II, step B the vinyl sulfone (6) is subjected to a stannylation reaction under conditions analogous to those described in Scheme I, step C to provide the (fluorovinyl)stannane described by structure (7).

The compounds of formula (I) wherein $R_3$ is ribose, 2'-deoxyribose or arabinose can be prepared as described in Scheme III. All substituents, unless otherwise indicated, are previously defined. The reagents and starting materials are readily available to one of ordinary skill in the art.

Scheme III

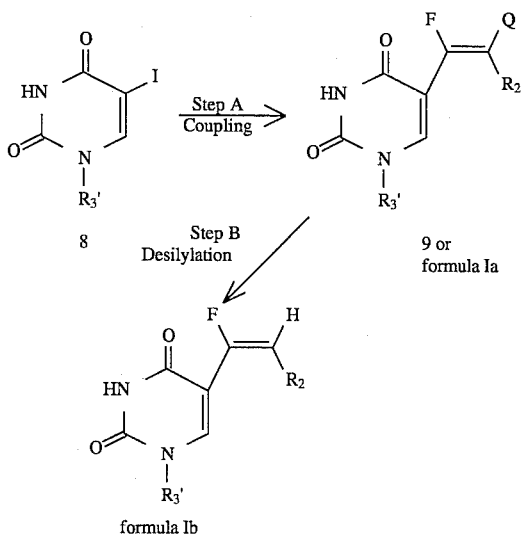

R$_3$' = ribose, 2'-deoxyribose or arabinose
Q = R$_1$ or Si(CH$_3$)$_3$
For formula Ia, Q = R$_1$
For (9), Q = Si(CH$_3$)$_3$ In Scheme III, step A the 5-iodo compound described by structure (8) wherein R$_3$' is ribose or 2'-deoxyribose is subjected to a coupling reaction with the (fluorovinyl)stannane compounds of either structure (4) or (7) prepared in Schemes I and II to provide the coupled product of either structure (9) or formula (Ia). For example, the 5-iodo compound (8) is dissolved in a suitable organic solvent, such as dimethyl formamide. A catalytic amount of a suitable catalyst is added. Examples of suitable catalysts are tetrakis(triphenylphosphine)palladium(O), bis(triphenylphosphine)palladium(II) chloride and the like. Approximately one equivalent of the (fluorovinyl)stannane (4) or (7) is added and the reaction is heated at a temperature of from about 40° to 125° C. for about 2 to 24 hours. The reaction is then cooled to room temperature and concentrated under vacuum. The residue is then purified by techniques well known in the art, such as flash chromatography on silica gel using a suitable eluent, such as methylene chloride/methanol to provide the coupled product (9) or formula (Ia).

In Scheme III, step B the coupled product described by structure (9) is desilylated to provide the compound of formula Ib. For example, the coupled product (9) is combined with one to five equivalents of oxalic acid in a suitable organic solvent, such as methanol. The reaction is stirred at room temperature from about 1 to 20 days. It is then filtered through a plug of silica gel and purified by techniques well known in the art, such as radial chromatography on a silica gel plate with a suitable eluent, such as methanol/methylene chloride to provide the compound of formula (Ib).

Alternatively, the desilylation can be accomplished by combining the coupled product (9) with an excess of potassium fluoride in a suitable organic solvent, such as dimethyl sulfoxide containing a catalytic amount of water. Alternatively, the coupled product (9) can be dissolved in tetrahydrofuran with a catalytic amount of water and treated with an excess of tetrabutylammonium fluoride. The reaction is heated at a temperature of from about 30° to 125° C. for about 6 to 24 hours. The reaction is then diluted with water and extracted with a suitable organic solvent, such as ethyl acetate. The combined organic extracts are dried over anhydrous magnesium sulfate, filtered and concentrated under vacuum. The residue is purified by techniques well known in the art, such as flash chromatography on silica gel with a suitable eluent, such as ethyl acetate/hexane to provide the compound of formula (Ib).

The compounds of formula (I) wherein R$_3$ is hydrogen can be prepared as described in Scheme IV. All substituents, unless otherwise indicated, are previously defined. The reagents and starting materials are readily available to one of ordinary skill in the art.

Scheme IV

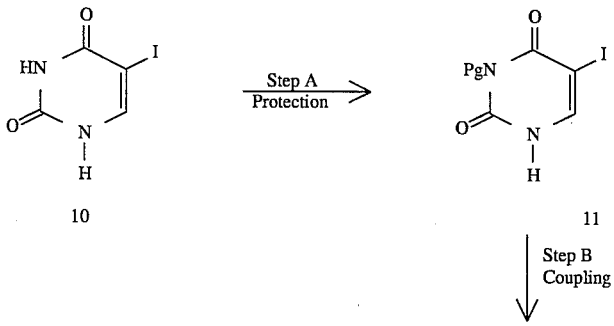

-continued
Scheme IV

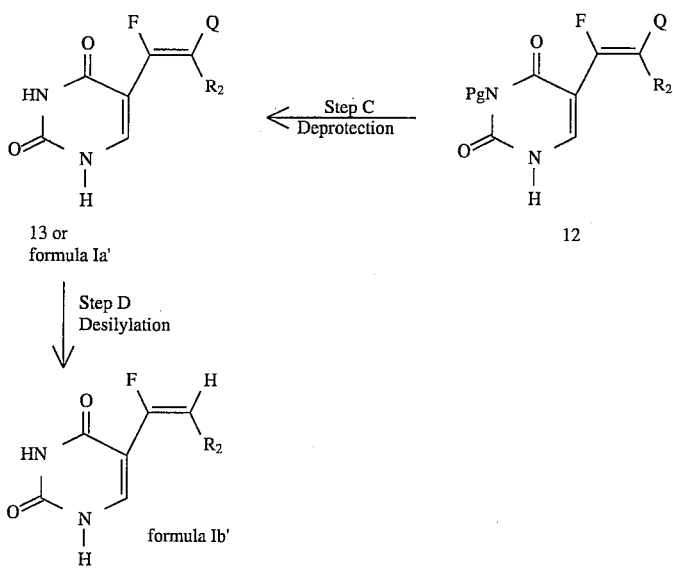

13 or
formula Ia'

Step D
Desilylation formula Ib'

Q = R₁ or Si(CH₃)₃
For formula Ia', Q = R₁
For (13), Q = Si(CH₃)₃

In Scheme IV, step A the 5-iodouracil of structure (10) wherein $R_3$ of formula I is hydrogen is protected with a suitable protecting group under conditions well known in the art to provide the $N^3$-protected compound described by structure (11). Examples of suitable protecting groups are 4-methoxylbenzyl, 3,5,5-trimethoxybenzyl, allyl and the like. The preferred protecting group is 4-methoxybenzyl. For example 5-iodouracil (10) is protected with a 4-methoxybenzyl group following the procedure of Van Aershot, A. and Herdewijn, L. J and P., *Tetrahedron Lett.*, 32(16), 1905, (1991). The 5-iodouracil is combined with 1.5 equivalents of triphenylphosphine and 1.5 equivalents of 4-methoxybenzyl alcohol in dioxane. To this is added 1.5 equivalents of dimethyl azodicarboxylate. The reaction is stirred for 24 hours and then quenched with water. The product is isolated and purified by techniques well known in the art. For example the reaction mixture is extracted with a suitable organic solvent, such as ethyl acetate. The combined organic extracts are dried over anhydrous magnesium sulfate, filtered and concentrated under vacuum. The residue is then purified by flash chromatography on silica gel with a suitable eluent, such as ethyl acetate/hexane to provide the $N^3$-protected compound (11).

In Scheme IV, step B the $N^3$-protected compound (11) is coupled to the (fluorovinyl)stannane of either structure (4) or (7) in a manner analogous to that described previously in Scheme III, step A to provide the coupled product described by structure (1.2).

In Scheme IV, step C the coupled product (12) is deprotected under conditions well known in the art to provide the deprotected compound described by structure (13) or formula Ia'. For example, following the procedure disclosed by Van Aershot, A. and Herdewijn, L. J and P., *Tetrahedron Lett.*, 32(16), 1905, (1991), the coupled product (12) is dissolved in aqueous acetonitrile and 3 equivalents of ceric ammonium nitrate is added at a temperature of from about 5° to 50° C. for about 1 to 18 hours. The product is then isolated by techniques well known in the art. For example the reaction is diluted with ethyl acetate, rinsed with water, brine, dried over anhydrous magnesium sulfate, filtered and concentrated under vacuum to provide the deprotected compound of structure (13) or formula (Ia').

In Scheme IV, step D the deprotected compound (13) is desilylated in a manner analogous to that described previously in Scheme III, step B to provide the compound described by formula (Ib').

An alternative method for the preparation of the compounds of formula (I) wherein $R_3$ is hydrogen is described in Scheme V. All substituents, unless otherwise indicated, are previously defined. The reagents and starting materials are readily available to one of ordinary skill in the art.

Scheme V

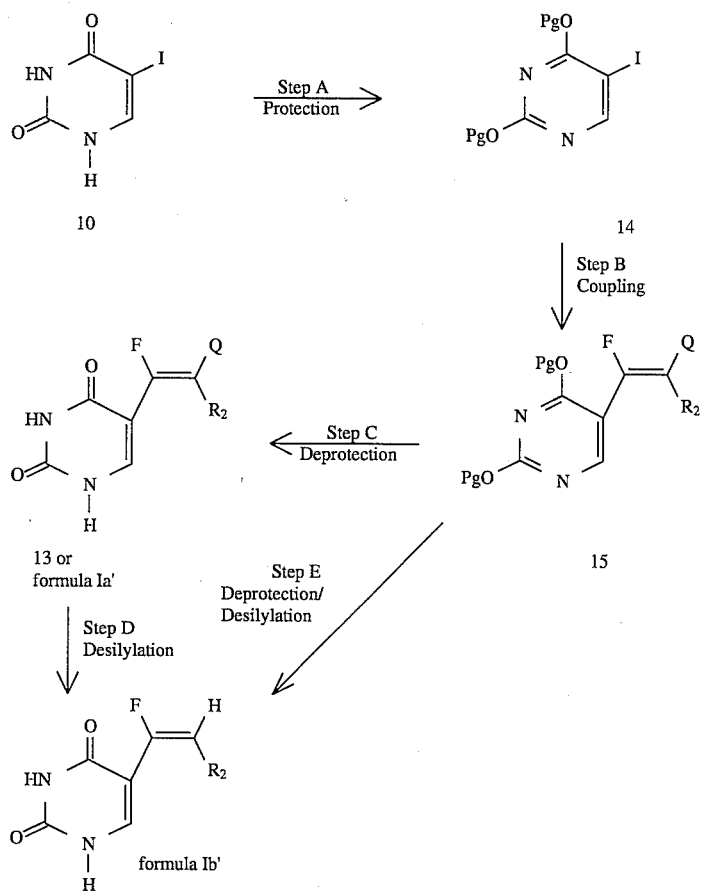

Q = R₁ or Si(CH₃)₃
For formula Ia', Q = R₁
For (13), Q = Si(CH₃)₃

In Scheme V, step A the 5-iodouracil of structure (10) wherein $R_3$ of formula (I) is hydrogen, is protected with a suitable protecting group under conditions well known in the art to provide the bis-$O^2,O^4$-protected uracil described by structure (14). Examples of suitable protecting groups are trimethylsilyl, t-butyldimethylsilyl, triphenylsilyl, t-butyldiphenylsilyl and the like. The preferred suitable protecting group is trimethylsilyl. For example 5-iodouracil (10) can be protected following generally the procedure of Ochi, K. et al. *Chem. Pharm. Bull.*, 33(4), 1703, (1985). The 5-iodouracil (10) is combined with excess trimethylchlorosilane or hexamethyldisilazane (HMDS) and heated to reflux for 1 to 5 hours. The reaction is then cooled and concentrated under vacuum to provide the bis-$O^2,O^4$-protected uracil of structure (14).

In Scheme V, step B the bis-$O^2,O^4$-protected uracil of structure (14) is coupled to the (fluorovinyl)stannane of either structure (4) or (7) in a manner analogous to that described previously in Scheme III, step A to provide the coupled product described by structure (15).

In Scheme V, step C the coupled product of structure (15) is deprotected under conditions well known in the art such as that described by T. W. Greene, "Protective Groups in Organic Synthesis", John Wiley & Sons, 1981, 40–50, to provide the deprotected compound described by structure (13) or formula (Ia'). For example the coupled product (15) is dissolved in a suitable solvent, such as tetrahydrofuran and then treated with a slight excess of a suitable fluoride ion source, such as tetrabutylammonium fluoride. The reaction is allowed to stir at room temperature for about 1 to 24 hours and the product is isolated by techniques well known in the art, such as filtration, extractive methods or flash chromatography. For example the reaction is diluted with ethyl acetate, rinsed with water, brine, dried over anhydrous magnesium sulfate, filtered and concentrated under vacuum to provide the deprotected compound of structure (13) or formula (Ia').

In Scheme V, step D the deprotected compound of structure (13) is desilylated in a manner analogous to that described previously in Scheme III, step B to provide the compound described by formula (Ib').

In Scheme V, step E the coupled product described by structure (15) wherein Q is Si(CH₃)₃, can be concomitantly deprotected and desilylated to provide the compound described by formula (Ib'). For example, the coupled product (15) wherein Q is Si(CH₃)₃, is dissolved in a suitable solvent, such as methanol and treated with one to 5 equivalents of oxalic acid. The reaction is stirred at room temperature for about 1 to 20 days. The product is then isolated by techniques well known in the art, such as filtration, extractive methods or flash chromatography. For example the reaction is diluted with ethyl acetate, rinsed with water, brine, dried over anhydrous magnesium sulfate, filtered and concentrated under vacuum to provide the compound of formula (Ib').

Alternatively, the concomitant deprotection and desilylation can be accomplished by combining the coupled product (15) wherein Q is $Si(CH_3)_3$, with an excess of potassium fluoride in a suitable organic solvent, such as dimethyl sulfoxide containing a catalytic amount of water. Alternatively, the coupled product (15) can be dissolved in tetrahydrofuran with a catalytic amount of water and treated with an excess of tetrabutylammonium fluoride. The reaction is heated at a temperature of from about 30° to 125° C. for about 6 to 24 hours. The reaction is then diluted with water and extracted with a suitable organic solvent, such as ethyl acetate. The combined organic extracts are dried over anhydrous magnesium sulfate, filtered and concentrated under vacuum. The residue is purified by techniques well known in the art, such as flash chromatography on silica gel with a suitable eluent, such as ethyl acetate/hexane to provide the compound of formula (Ib).

Compounds of formula (I) wherein $R_3$ is hydrogen can also be prepared as described in Scheme VI. All substituents, unless otherwise indicated, are previously defined. The reagents and starting materials are readily available to one of ordinary skill in the art.

m-chloroperbenzoic acid (MCPBA) oxidation of the intermediate α-fluorothioether to provide the α-fluorosulfoxide (17). For example, see Robins, M. J.; Wnuk, S. F., *J. Org. Chem.*, 58, 3800 (1993) which discloses the efficient conversion of thioethers to α-fluorothioethers with DAST-$SbCl_3$ and subsequent oxidation with MCPBA.

Alternatively, in step A1, the phenyl sulfide (16) can be converted to the phenyl sulfoxide described by structure (16a) followed by fluorination/oxidation to provide α-fluorosulfoxide (17). For example, approximately an equivalent of a suitable oxidizing agent, such as sodium periodate dissolved in water is combined with the phenyl sulfide (16) dissolved in a suitable organic solvent, such as methanol at about 0° C. with stirring. The reaction is stirred for about one hour, warmed to room temperature and then diluted with a suitable organic solvent, such as chloroform. The organic layer is separated and then rinsed with brine, dried over anhydrous magnesium sulfate, filtered and concentrated under vacuum. The residue can be purified by flash chromatography on silica gel with a suitable eluent such as ethyl acetate/hexane to provide the phenyl sulfoxide (16a).

In step A2, the phenyl sulfoxide (16a) is converted to the α-fluorosulfoxide (17) by a fluoro-Pummerer rearrangement [see for example Hudlicky, M., *Org. React.*, 35, 513, (1988)] with DAST followed by oxidation. For example, phenyl Scheme VI

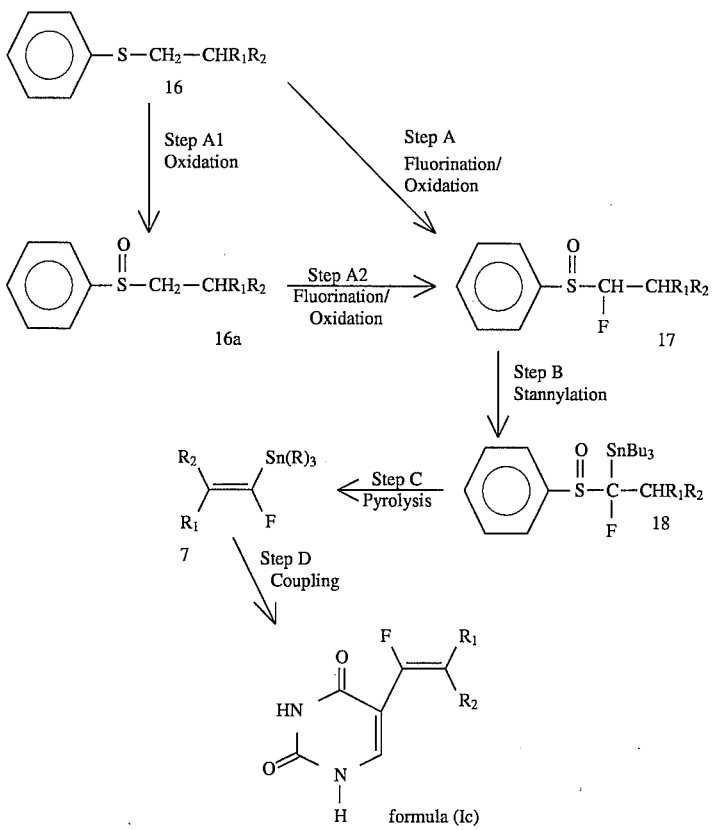

In Scheme VI, the phenyl sulfide of structure (16) can be converted to the α-fluorosulfoxide described by structure (17) following either step A or steps A1 and A2.

In step A the phenyl sulfide (16) can be converted to the α-fluorothioether with diethylaminosulfur trifluoride-antimony trichloride [DAST-$SbCl_3$] catalysis followed by sulfoxide (16a) is dissolved in a suitable organic solvent, such as chloroform under an inert atmosphere, such as nitrogen. To this solution is added about 0.1 equivalents of antimony trichloride. After the antimony trichloride dissolves, an excess of diethylaminosulfur trifluoride (DAST) is added to the solution and the reaction is allowed to stir for about 1 to 3 hours at room temperature. The reaction is then diluted with a suitable organic solvent, such as chloroform and then washed with saturated sodium bicarbonate, brine, dried over anhydrous sodium sulfate and filtered. The filtrate is then cooled to about −20° C. and treated with an equivalent of a suitable oxidizing agent, such as m-chloroperbenzoic acid. The reaction is allowed to stir at −20° C. for about 1 hour. The α-fluorosulfoxide (17) is then isolated and purified by techniques well known in the art. For example, the reaction is washed with saturated sodium bicarbonate to which sodium bisulfite has been added, then saturated sodium bicarbonate, brine, dried over anhydrous sodium sulfate, filtered and concentrated under vacuum. The residue is then purified by flash chromatography on silica gel using a suitable eluent, such as ethyl acetate/hexane to provide the α-fluorosulfoxide (17).

Alternatively, the phenyl sulfoxide (16a) can be converted to the α-fluorosulfoxide (17) by generating the carbanion of phenyl sulfoxide (16a) with n-butyllithium followed by treatment with about 1.5 equivalents of N-fluorobenzenesulfonamide (NFSI; information regarding availability of NFSI can be obtained from G. A. Shia, Allied Signal Inc., Buffalo Research Laboratory, Buffalo, N.Y., 14210) at −60° C. for 30 minutes and then at room temperature for 2 hours. The α-fluorosulfoxide (17) is then isolated and purified by techniques well known in the art.

In step B, the α-fluorosulfoxide (17) is stannylated to provide the α-stannylsulfoxide (18). For example, the α-fluorosulfoxide (17) is dissolved in a suitable organic solvent, such as tetrahydrofuran to which is added about 1.1 equivalents of a trialkyltin iodide, such as tributyltin iodide. This solution is then added dropwise to a stirring solution of 2 equivalents of lithium diisopropylamide in tetrahydrofuran at about −70° C. The reaction is then allowed to stir for about 15 to 30 minutes and is then partitioned between ether and 5% sodium thiosulfate. The α-stannylsulfoxide (18) is then isolated and purified by techniques well known in the art. For example, the organic layer is separated, dried over anhydrous magnesium sulfate, filtered and concentrated under vacuum. The residue is then purified by flash chromatography on silica gel using a suitable eluent, such as ethyl acetate/hexane to provide the α-stannylsulfoxide (18).

In step C, the α-stannylsulfoxide (18) is subjected to a pyrolysis reaction to provide the (fluorovinyl)stannane (7). For example, the α-stannylsulfoxide (18) is dissolved in a suitable organic solvent, such as toluene. An excess of Hunig's base (N,N-diisopropylethylamine) is added to the solution which is then heated at about 100°–110° C. for 1–4 hours under an inert atmosphere, such as argon. After cooling the solvent is removed under vacuum and the (fluorovinyl)stannane (7) is purified by techniques well known in the art. For example, flash chromatography on silica gel using a suitable eluent, such as hexane provides the (fluorovinyl)stannane (7).

In step D, the (fluorovinyl)stannane (7) is coupled to to 5-iodouracil to provide the compound of formula (Ic). For example, 5-iodouracil is combined with about 1.25 equivalents of the (fluorovinyl)stannane (7) and a catalytic amount of tetrakis(triphenylphosphine)palladium(O) in a suitable organic solvent, such as dimethylformamide (DMF). The mixture is heated at about 100° C. for about 2 hours under an atmosphere of nitrogen. After cooling, the solvent is then removed under high vacuum and the residue is purified by techniques well known in the art, such as flash chromatography or recrystallization. For example, the residue is purified by flash chromatography on silica gel using a suitable eluent, such as methanol/methylene chloride. The product can then be further purified by recrystallization from a suitable solvent, such as water to provide the compound of formula (Ic).

The relative configurations encompassed by the stereoisomers of formula (I) are readily prepared by one skilled in the art. In addition, the enantiomers of formula (I) can be resolved utilizing techniques well known in the art of chemistry such as crystallization techniques described by Jacques, J. et al. "Enantiomers, Racemates, and Resolutions", John Wiley and Sons, Inc., 1981 or by chiral column chromatography.

The following examples present typical syntheses as described by Schemes I, II, III, IV and V. These examples are understood to be illustrative only and are not intended to limit the scope of the invention in any way. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor and "δ" refers to parts per million down field from tetramethylsilane.

EXAMPLE 1

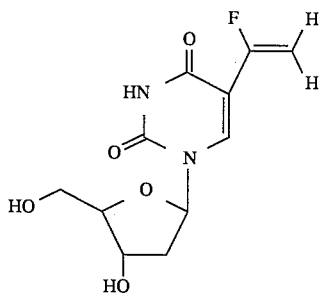

Preparation of 2'-deoxy-5-(1-fluoroethenyl)uridine

Scheme I, step A; Dissolve oxalyl chloride (13.9 mL, 159 mmol) in dichloromethane (500 mL) and cool the solution to −79° C. under an atmosphere of nitrogen. Add dimethyl sulfoxide (12.8 mL dissolved in 250 mL of dichloromethane, 180 mmol) dropwise over 20 minutes. After addition is complete stir the reaction for an additional 10 minutes and add trimethylsilylmethanol (13.9 mL dissolved in 150 mL of dichloromethane, 110 mmol). Stir the reaction for 15 minutes at −78° C. and add triethylamine (55 mL, 392 mmol). Stir the reaction for an additional 20 minutes at −78° C. after addition is complete to produce the aldehyde already in solution for the olefination reaction.

Scheme I, step B; Dissolve fluoromethylphenyl sulfone (18.45 g, 106 mmol) in anhydrous tetrahydrofuran (400 mL) under an atmosphere of nitrogen and cool the solution to −78° C. Add sequentially lithium diisopropylamide (191 mL of 1.0M solution in tetrahydrofuran) and diethyl chlorophosphate (15.3 mL, 106 mmol) and 'stir the reaction for 1.5 hours at −78° C. Add this solution via cannula to the above prepared aldehyde already in solution and stir the reaction at −78° C. for one hour. Then allow the reaction to warm to room temperature and stir for an additional hour. Then quench the reaction with saturated ammonium chloride. Separate the phases and extract the aqueous phase with chloroform (3×). Combine the organic phase and organic extracts and dry over anhydrous magnesium sulfate, filter and concentrate under vacuum. Purify the residue by flash chromatography (ethyl acetate/hexane, 1:5, silica gel) to provide the fluorovinyl sulfone (21.2 g, 77%) as a 10:3 mixture of E/Z isomers.

Scheme I, step C; Dissolve the above prepared fluorovinyl sulfone (21.2 g, 82 mmol) in toluene (400 mL) under an atmosphere of nitrogen. Add azoisobutyronitrile (670 mg, 4.1 mmol, AIBN) and tributyltin hydride (48.5 mL, 180 mmol). Heat the reaction at reflux for 24 hours. Cool the reaction and concentrate under vacuum. Purify the residue by flash chromatography (hexane, silica gel) to provide the (fluorovinyl)stannane (30.4 g, 91%).

Scheme III, step A; Combine 5-iodo-2'-deoxyuridine (2.35 g, 6.6 mmol), tetrakis(triphenylphosphine)palladium(O) (100 mg) and the above prepared (fluorovinyl)stannane (2.6 g, 6.7 mmol) in dimethylformamide (80 mL). Heat the reaction at 100° C. for 24 hours and then cool to room temperature. Concentrate the reaction under high vacuum and purify the residue by flash chromatography (methylene chloride/methanol, 9:1, silica gel) to provide the coupled product (200 mg).

Scheme III, step B; Combine oxalic acid (140 mg, 1.6 mmol) and the above formed coupled product (200 mg) in methanol (10 mL). Stir the reaction for 9 days at room temperature. Then filter the reaction through a plug of silica gel (25% methanol/methylene chloride). Concentrate the filtrate under vacuum and purify the residue by radial chromatography (4% methanol/methylene chloride, 2 mm plate, silica gel) to provide the title compound (88.6 mg, 72%), HRMS Calcd. 271.0730, Found 271.0728.

EXAMPLE 2

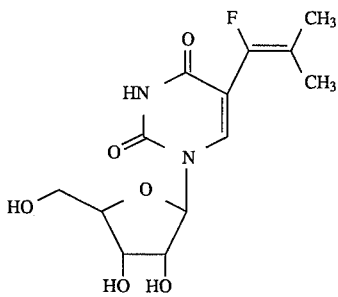

Preparation of
5-(1-fluoro-2,2-dimethyl-ethenyl)uridine

Scheme II, step A; Dissolve fluoromethylphenyl sulfone (6 g, 34.5 mmol) in anhydrous tetrahydrofuran (100 mL, THF) and cool to −78° C. Add diethyl chlorophosphate (5.2 mL, 36 mmol) and then add lithium hexamethyldisilamide (45 mL of a 1M solution in THF, 45 mmol). After one hour at −78° C. acetone (3.5 g, 60 mmol) is added and the reaction is allowed to warm to room temperature. It is then quenched with saturated ammonium chloride and concentrated under vacuum to remove tetrahydrofuran. The remaining aqueous is extracted with methylene chloride (2×200 mL). The combined organic extracts are dried over anhydrous magnesium sulfate, filtered and concentrated. The residue is purified by flash chromatography (ethyl acetate/hexane, 1:7, silica gel) to provide the vinyl sulfone (4.2 g).

Scheme II, step B; Dissolve the above prepared vinyl sulfone (4.0 g, 18.7 mmol) in toluene (100 mL) and add tributyltin hydride (11.9 g, 41 mmol) and azoisobutyronitrile (25 mg, AIBN). Heat the reaction to 80° C. overnight and then concentrate under vacuum. Purify the residue by flash chromatography (hexane, silica gel) to provide the desired stannylated product (4.91 g, 72%).

Scheme III, Step A; Combine 5-iodouridine (370 mg, 1 mmol), tetrakis(triphenylphosphine)palladium(O) (15 mg) and the above prepared stannylated product (360 mg, 1 mmol) in dimethylformamide (10 mL). Heat the reaction at 100° C. for 24 hours and then cool to room temperature. Concentrate the reaction under high vacuum and purify the residue by flash chromatography (methylene chloride:methanol:ammonium hydroxide, 90:10:1) to provide the title compound (74 mg) as a colorless oil; HRMS Calcd. 316.1071, Found 316.1085.

EXAMPLE 3

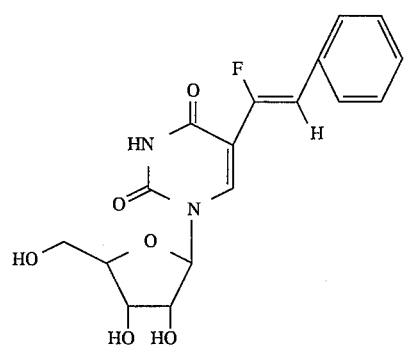

Preparation of
(E)-5-(1-fluoro-2-phenyl-ethenyl)uridine

Scheme II, step A; Dissolve fluoromethylphenyl sulfone (10 g, 57 mmol) in anhydrous tetrahydrofuran (200 mL) and cool the solution to −78° C. Add diethyl chlorophosphate (9.8 g, 57 mmol) and then lithium hexamethyldisilamide (106 mL of a 1M solution in THF, 106 mmol). After 45 minutes add benzaldehyde (4 g, 38 mmol) and allow the reaction to warm to room temperature. Quench the reaction with saturated ammonium chloride and extract with ethyl acetate (2×150 mL). Dry the combined organic extracts over anhydrous magnesium sulfate, filter and concentrate under vacuum. Purify the residue by flash chromatography (ethyl acetate/hexane, 1:5, silica gel) to provide the desired vinyl sulfone (9.48 g, 95%) as a white solid.

Scheme II, step B; Combine the above prepared vinyl sulfone (8.9 g, 34 mmol), tributyltin hydride (21.7 g, 75 mmol) and AIBN (100 mg) in toluene (200 mL). Heat the reaction at 60° C. overnight. Add an additional amount of AIBN (100 mg) and heat at 80° C. for 7 hours. Cool the reaction and concentrate under vacuum. Purify the residue by flash chromatography (hexane, silica gel) to provide the desired stannylated product (13.9 g) as a colorless oil.

Scheme III, step A; Combine 5-iodouridine (320 mg, 0.86 mmol), tetrakis(triphenylphosphine)palladium(O) (10 mg) and the above prepared stannylated product (355 mg, 0.86 mmol) in dimethylformamide (20 mL). Heat the reaction at 50° C. for 3 hours and then heat the reaction at 100° C. for 24 hours. Cool the reaction to room temperature. Concentrate the reaction under high vacuum and purify the residue by flash chromatography (ethyl acetate, silica gel) followed by recrystallization from acetonitrile to provide the title compound (51 mg) as crystals.

EXAMPLE 4

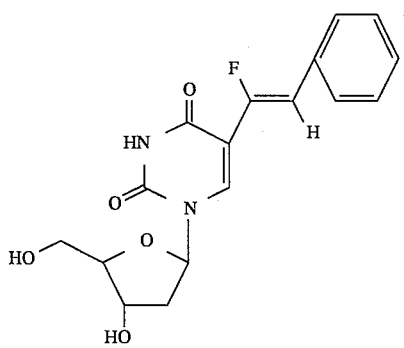

Preparation of
(E)-2'-deoxy-5-(1-fluoro-2-phenyl-ethenyl)uridine

Scheme II, step A; Combine 5-iodo-2'-deoxyuridine (500 mg, 1.41 mmol), tetrakis(triphenylphosphine)palladium(O) (10 mg) and the stannylated product prepared in example 3, Scheme II step B (580 mg, 1.41 mmol) in dimethylformamide (20 mL). Heat the reaction at 100° C. for 24 hours. Cool the reaction to room temperature. Concentrate the reaction under high vacuum and purify the residue by flash chromatography (methylene chloride:methanol:ammonium hydroxide, 90:10:1, silica gel) followed by recrystallization from acetonitrile to provide the title compound as a white solid, mp foams at 212°–215° C. to give a white solid with mp<250° C.

EXAMPLE 5

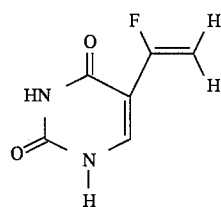

Preparation of 5-(1-fluoroethenyl)uracil

Scheme IV, step A; Following the procedure described by Van Aershot, A. and Herdewign, P. , *Tetrahedron Lett.*, 72(16), 1905, (1991), combine 5-iodouracil (3.07 g, 12.9 mmol), triphenylphosphine (5 g, 19.3 mmol) and 4-methoxybenzyl alcohol (2.7 g, 19.3 mmol) in dioxane (50 mL) with stirring. Slowly add via syringe dimethyl azodicarboxylate (2.8 g, 19.3 mmol). Stir the reaction for 24 hours and quench with water. Extract the quenched reaction mixture with ethyl acetate. Dry the organic extract over anhydrous magnesium sulfate, filter and concentrate under vacuum. Purify the residue by flash chromatography (30% ethyl acetate/hexane, silica gel) to provide the protected 5-iodouracil (3.3 g).

Scheme IV, step B; Combine the above protected 5-iodouracil (2.3 g, 6.5 mmol), bis(triphenylphosphine)palladium(II) chloride (100 mg), the (fluorovinyl)stannane prepared in example 1, Scheme I, step C (7.7 mmol) in toluene (20 mL). Heat the reaction at 100° C. for 24 hours. Cool the reaction and concentrate under vacuum. Purify the residue by flash chromatography (ethyl acetate/hexane, 1:3, silica gel) to provide the coupled product (900 mg) as a white solid.

Scheme IV, step C; Dissolve the above prepared coupled product (3 mmol) in aqueous acetonitrile, cool the solution to approximately 5° C. and treat with ceric ammonium nitrate (9 mmol). Stir the reaction for 24 hours. Then dilute the reaction with ethyl acetate and rinse with water, brine, dry over anhydrous magnesium sulfate, filter and concentrate to provide the deprotected uracil.

Scheme IV, step D; Combine oxalic acid (1.6 mmol) and the above formed deprotected uracil (1.6 mmol) in methanol (10 mL). Stir the reaction for 9 days at room temperature. Then filter the reaction through a plug of silica gel (25% methanol/methylene chloride). Concentrate the filtrate under vacuum and purify the residue by radial chromatography (4% methanol/methylene chloride, 2 mm plate, silica gel) to provide the title compound.

Alternative Procedure for the Preparation of 5-(1-fluoroethenyl)uracil as shown in Scheme V Scheme V, step A; Following generally the procedure described by Ochi, K. et al. *Chem. Pharm. Bull.*, 33(4), 1703, (1985), combine 5-iodouracil (5 mmol) with hexamethyldisilazane (15 mL) and heat at reflux for 3 hours. Allow the reaction to cool and concentrate under vacuum to provide the bis-$O^2,O^4$-protected 5-iodouracil.

Scheme V, step B; Combine the above bis-$O^2,O^4$-protected 5-iodouracil (6.5 mmol), bis(triphenylphosphine)palladium(II) chloride (100 mg), the (fluorovinyl)stannane prepared in example 1, Scheme I, step C (7.7 mmol) in toluene (20 mL). Heat the reaction at 100° C. for 24 hours. Cool the reaction and concentrate under vacuum. Purify the residue by flash chromatography (ethyl acetate/hexane, 1:3, silica gel) to provide the coupled product.

Scheme V, step C; Dissolve the above prepared coupled product (5 mmol) in tetrahydrofuran (10 mL) and treat with tetrabutylammonium fluoride (22 mmol). Stir at 0° C. for 10 minutes. Dilute the reaction with ethyl acetate, rinse with water, brine, dry over anhydrous magnesium sulfate, filter and concentrate under vacuum to provide the deprotected uracil.

Scheme V, step D; Combine oxalic acid (1.6 mmol) and the above formed deprotected uracil (1.6 mmol) in methanol (10 mL). Stir the reaction for 9 days at room temperature. Then filter the reaction through a plug of silica gel (25% methanol/methylene chloride). Concentrate the filtrate under vacuum and purify the residue by radial chromatography (4% methanol/methylene chloride, 2 mm plate, silica gel) to provide the title compound.

Scheme V, step E; Combine oxalic acid (6 mmol) and the above formed deprotected uracil (1.6 mmol) in methanol (10 mL). Stir the reaction for 10 days at room temperature. Then filter the reaction through a plug of silica gel (25% methanol/methylene chloride). Concentrate the filtrate under vacuum and purify the residue by radial chromatography (4% methanol/methylene chloride, 2 mm plate, silica gel) to provide the title compound.

Alternative Procedure for the Preparation of 5-(1-fluoroethenyl)uracil as shown in Scheme VI Scheme VI, step A1; A solution of sodium periodate (40.9 g, 191 mmol) in water (400 mL) is cooled to 0° C. under an atmosphere of nitrogen. A solution of phenyl ethyl sulfide (25.22 g, 183 mmol) in methanol (400 mL) is added to the stirring solution of sodium periodate over 20 minutes. The reaction is stirred at 0° C. for one hour and is then allowed to warm to room temperature. The reaction is then extracted with chloroform. The combined organic extracts are washed with brine, dried over anhydrous magnesium sulfate, filtered and concentrated under vacuum. The residue is purified by flash chromatography (50% to 70% ethyl acetate/hexane, silica gel) to provide the sulfoxide (26.18 g, 93%).

Scheme VI, step A2: The above prepared sulfoxide (1.54 g, 10 mmol) is dissolved in chloroform (50 mL) under an atmosphere of nitrogen. To this solution is added antimony trichloride (228 mg, 1 mmol). After the antimony trichloride dissolves, diethylaminosulfur trifluoride (2.65 mL, 20 mL, DAST) is added by syringe. The reaction is then allowed to stir at room temperature for one hour. The reaction is then diluted with chloroform (100 mL) and washed with saturated sodium bicarbonate (100 mL with 5 g sodium hydroxide), saturated sodium bicarbonate (100 mL) and then brine (100 mL). The aqueous layer is then back extracted with chloroform (100 mL). The combined organic extracts are dried over anhydrous sodium sulfate and filtered. The filtrate is then cooled to –20° C. and treated with m-chloroperbenzoic acid (3.51 g, 10 mmol, 50%). The reaction is stirred at –20° C. for one hour. The reaction is then washed with saturated sodium bicarbonate (100 mL with 10 g sodium bisulfate added), saturated sodium bicarbonate (100 mL), brine (100 mL), dried over anhydrous sodium sulfate, filtered and concentrated under vacuum. The residue is purified by flash chromatography (25% ethyl acetate/hexane to provide the α-fluorosulfoxide (1.55 g, 90%).

Scheme VI, step B: Diisopropylamine (2.8 mL, 20 mmol) is dissolved in tetrahydrofuran (45 mL, THF) under an atmosphere of argon and cooled to –5° C. A solution of n-butyllithium (8 mL, 20 mmol, 2.5M in hexane) is added dropwise to the stirring solution which is then allowed to stir for 10 minutes. The solution is then cooled to –70° C. A solution of the above prepared α-fluorosulfoxide (1.72 g, 10 mmol) and tributyltin iodide (3.14 mL, 11 mmol) in tetrahydrofuran (5 mL) is added dropwise to the solution keeping the temperature below –60° C. After addition is complete, the pale yellow chalky mixture is stirred for 15 minutes and then partitioned between ether and 5% sodium thiosulfate. The organic layer is separated, dried over anhydrous magnesium sulfate, filtered and concentrated under vacuum. The residue is purified by flash chromatography (6% ethyl acetate/hexane, silica gel, $R_f$=0.19, 0.24) to provide the α-stannylsulfoxide (1.60 g, 35%) as a 2:1 mixture of diastereomers: $^{19}F$ NMR (CDCl$_3$) δ –166.99 (m, major), –167.57 (m, minor).

Scheme VI, step C: The above prepared α-stannylsulfoxide (0.46 g, 1 mmol) is dissolved in toluene (10 mL) with N,N-diisopropylethylamine (1 mL, 5.74 mmol). The solution is heated at 110° C. for 2 hours under an atmosphere of argon. The mixture is then cooled and the solvent removed under vacuum. The residue is purified by flash chromatography (hexane, silica gel, $R_f$=0.8) to provide the (fluorovinyl)stannane (165 mg, 50%) as an oil; $^1H$ NMR (CDCl$_3$, 500 MHz) δ 0.90 (t, 9H, J=7.3 Hz), 1.01 (m, 6H), 1.33 (m, 6H), 1.54 (m, 6H), 4.55 (m, 1H, $J_{H-H}$=2.8 Hz, $J_{H-F}$= 38.1 Hz, $J_{H-Sn}$=67.0, 69–8 Hz), 5.31 (m, 1H, $J_{H-H}$=2.8 Hz, $J_{H-F}$=67.6 Hz, $J_{H-Sn}$=15.1 Hz): $^{19}F$ NMR (CDCl$_3$, 470 MHz) δ –84.77 (m, dd, (84%), J=38.1, 67.6 Hz), J=(7.6%)$_{F-}$117$_{Sn}$, J=(8.6%)$_{F-}$119$_{Sn}$, =228, 238 Hz; $^{13}C$ NMR (CDCl$_3$, 76 MHz) δ 9.91 ($J_{F-C}$=2.0 Hz, $J_{Sn-C}$=338.8, 354.3 Hz), 13.63, 27.15 ($J_{Sn-C}$= 57.4 Hz), 28.80 ($J_{Sn-C}$=21.6 Hz), 107.59 ($J_{F-C}$=1.6 Hz, $J_{Sn-C}$= 64.2 Hz), 178.92 ($J_{F-C}$=319.5 Hz).

Scheme VI, Step D; 5-iodouracil (340 mg, 1.43 mmol), the (fluorovinyl)stannane (600 mg, 1.8 mmol, prepared above in step C), tetrakis(triphenylphosphine)palladium(O) (approximately 20 mg) and dimethylformamide (4 mL) are combined and heated at 100° C. for 2 hours under an atmosphere of nitrogen. The reaction is then cooled to room temperature and the solvent removed under high vacuum. The residue is purified by flash chromatography (8% methanol/methylene chloride). The fraction containing the product is azeotroped with methylene chloride and then slurried in methylene chloride/ether. The solid is collected by filtration and then recrystallized from water (3 mL) to provide after filtration a light tan solid (60.5 mg). The filtrate is concentrated under vacuum and the residue is purified by radial chromatography (6% methanol/methylene chloride) to provide an additional 10 mg to provide a total of 70.5 mg (45%) of title compound. This is combined with 70 mg from another similar run and then purified again by radial chromatography (6% methanol/methylene chloride) to provide 91 mg of title compound as a buff colored solid after drying under high vacuum; mp 235°–238° C.

5-Fluorouracil (5-FU) is readily available and its use as an antineoplastic agent is well known and appreciated in the art [For example, See Corr, R. T., and Fritz, W. L., "CANCER CHEMOTHERAPY HANDBOOK", 1980, Elseveir North Holland, Inc., New York, N.Y. and Calabresi, P., and Chabner, B. A., "CHEMOTHERAPY OF NEOPLASTIC DISEASES", Section XII, GOODMAN AND GILLMAN'S THE PHARMACOLOGICAL BASIS OF THERAPEUTICS, 8th ed., 1990, Pergamon Press Inc., Elmsford, N.Y.].

The present invention provides a method of treating a patient suffering from a neoplastic disease state comprising administering to said patient an effective antineoplastic amount of a compound of formula (I).

The term "neoplastic disease state" as used herein refers to an abnormal state or condition characterized by rapidly proliferating cell growth or neoplasm. Neoplastic disease states for which treatment with a compound of formula (I) will be particularly useful include: Leukemias such as, but not limited to, acute lymphoblastic, chronic lymphocytic, acute myeloblastic and chronic myelocytic; Carcinomas and adenocarcinomas, such as, but not limited to, those of the cervix, esophagus, stomach, small intestines, colon, lungs (both small cell and large cell), breast and prostate; Sarcomas, such as, but not limited to, oesteroma, osteosarcoma, lepoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease. Neoplastic disease states for which treatment with a compound of formula (I) will be particularly preferred include carcinomas and adenocarcinomas, particularly of the breast, prostate and lung.

As used herein, the term "patient" refers to a warm-blooded animal, such as a mammal, which is afflicted with a particular neoplastic disease state. It is understood that humans, mice and rats are included within the scope of the term "patient".

An effective antineoplastic amount of a compound of formula (I) refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific neoplastic disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective amount of a compound of formula (I) is expected to vary from about 0.1 milligram per kilogram of body weight per day (mg/kg/day) to about 100 mg/kg/day. Preferred amounts are expected to vary from about 0.5 to about 10 mg/kg/day.

In addition, the present invention provides a method of treating a patient suffering from a neoplastic disease state comprising conjunctive therapy with an effective antineoplastic amount of a compound of formula (I) and an effective antineoplastic amount of 5-fluorouracil. This conjunctive therapy provides a synergistic antineoplastic effect.

Conjunctive therapy with a compound of formula (I) and 5-fluorouracil will be particularly effective in the treatment of a patient afflicted with breast, colon, stomach, pancreas, ovary, head and neck carcinoma, urinary bladder carcinoma and premalignant skin lesions.

In effecting treatment of a patient afflicted with a neoplastic disease state as described above, a compound of formula (I) is administered in conjunctive therapy with 5-fluorouracil. As used herein, the term "conjunctive therapy" contemplates co-administration of a compound of formula (I) along with 5-fluorouracil. This co-administration may take place at essentially the same time, it may take place sequentially, or it may take place alternately.

In providing co-administration at essentially the same time, the courses of treatment with a compound of formula (I) and 5-fluorouracil run essentially concomitantly. In providing sequential co-administration, a full course of treatment of one of the agents is terminated and then followed by a full course of treatment of the other. In providing alternate co-administration, a partial course of treatment of one of the agents is terminated and then followed by a partial course of treatment of the other in an alternating manner until a full treatment of each agent is administered. When the compound of formula (I) and 5-fluorouracil are co-administered in a sequential or an alternate manner, it is generally preferred to administer the compound of formula (I) first and 5-fluorouracil last.

In effecting the conjunctive therapy according to the present invention, it is preferred to co-administer the compound of formula (I) and 5-flurouracil in a sequential or an alternate manner. It is most preferred to co-administer the compound of formula (I) and 5-flurouracil in a sequential manner.

The effective antineoplastic amounts of 5-flurouracil are well known and appreciated in the art. For example, an effective antineoplastic amount of 5-fluorouracil (5-FU) is expected to vary from about 6 mg/m$^2$/day to about 800 mg/m$^2$/day.

In effecting treatment of a patient afflicted with a disease state described above, the compounds of formula (I) can be administered in combination with 5-fluorouracil in the proportions of antineoplastic amount of a compound of formula (I) to antineoplastic amount of 5-fluorouracil in the range of about 1:0.1 to about 1:50, more preferably in the range of about 1:1 to about 1:20 and most preferably in the range of about 1:1 to about 1:10.

5-Fluorouracil can be administered in a manner as is well known and accepted in the art. For example, 5-fluorouracil may be administered intravenously.

The present invention further provides a method of inhibiting thymidylate synthetase in a patient in need thereof comprising administering to said patient an effective inhibitory amount of a compound of formula (I).

It is understood that patients suffering from neoplastic disease states are in need of a thymidylate synthetase inhibitor such as a compound of formula (I).

Administration of a compound of formula (I) to a patient results in inhibition of thymidylate synthetase in the patient. Thus, by treatment of a patient with a compound of formula (I) neoplastic disease states are inhibited or suppressed.

A patient is in need of treatment with an agent which inhibits thymidylate synthetase, such as a compound of formula (I), where the patient is suffering from certain neoplastic diseases states for which elevated activity of thymidylate synthetase is implicated as a contributing factor in the progression of the disease.

Based on standard clinical and laboratory tests and procedures, an attending diagnostician, as a person skilled in the art, can readily identify those patients who are in need of treatment with an agent which inhibits thymidylate synthetase, such as a compound of formula (I).

An effective inhibitory amount of a compound of formula (I) is that amount which is effective, upon single or multiple dose administration to a patient, in providing an inhibition of thymidylate synthetase.

An effective inhibitory amount of a compound of formula (I) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific neoplastic disease involved; the degree of or involvement or the severity of the disorder; the response of the individual patient; the particular compound administered; the mode of administration; the bioavailability characteristics of the preparation administered; the dose regimen selected; the use of concomitant medication; and other relevant circumstances.

An effective inhibitory amount of a compound of formula (I) is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a disease state described above, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, the form of administration of 5-fluorouracil, the manner of co-administration selected, and other relevant circumstances.

The compounds of formula (I) can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (I) in admixture or otherwise in association with one or more inert carriers. These compositions are useful, for example, as assay standards, as convenient means of making bulk shipments, or as pharmaceutical compositions. An assayable amount of a compound of formula (I) is an amount which is readily measurable by standard assay procedures and techniques as are well known and appreciated by those skilled in the art. Assayable amounts of a compound of formula (I) will generally vary from about 0.001% to about 75% of the composition by weight. Inert carriers can be any material which does not degrade or otherwise covalently react with a compound of formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, capsules, troches, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formula (I).

With respect to the substituent $R_3$, compounds of the formula (I) wherein $R_3$ is 2'-deoxyribose are generally preferred.

The following list illustrates compounds according to the present invention:

1) 2'-deoxy-5-(1-fluoroethenyl)uridine;

2) 5-(1-fluoro-2,2-dimethyl-ethenyl)uridine;

3) (E)-5-(1-fluoro-2-phenyl-ethenyl)uridine;

4) (E)-2'-deoxy-5-(1-fluoro-2-phenyl-ethenyl)uridine;

5) 5-(1-fluoroethenyl)uracil;

6) 1-arabinosyl-5-(1-fluoroethenyl)uracil.

The following example is provided in order to illustrate the method of use of the present invention. This example is intended to be illustrative only and is not to be construed so as to limit the scope of the invention in any way.

EXAMPLE 6

Synergistic Antiproliferative Activity of 2'-Deoxy-5-(1-fluoroethenyl)-uridine in Combination with 5-Fluorouracil Against KB Cells Plate KB cells ($2 \times 10^3$ cells/well) and allow to grow for 18 hours. Treat with 2'-deoxy-5-(1-fluoroethenyl)uridine (15 ng/mL) for 24 hours. Wash the compound and expose cells to 5-fluorouracil for another 72 hours. Determine the cell viability by a colorimetric assay, essentially as described by Carmichael et al. [*Cancer Res.* 47, 936 (1987)], whereby the cellular reduction of MTT [3-(4,5-dimethylthiazol-2-yl)-2, 5-diphenyltetrozolium bromide] is measured.

Calculate $IC_{50}$ values for the individual treatments as well as for the combined treatments of 2'-deoxy-5-(1-fluoroethenyl)-uridine with 5-fluorouracil. The $IC_{50}$ values at the various concentrations of 2'-deoxy-5-(1-fluoroethenyl)-uridine alone, 5-fluorouracil alone and 2'-deoxy- 5-(1-fluoroethenyl)-uridine alone in combination with -fluorouracil are presented in Table 1.

TABLE 1

Synergistic Antitumor Activity of 2'-Deoxy-5-(1-fluoroethenyl)-uridine in Combination with 5-Fluorouracil Against KB Cells

| Treatment | $IC_{50}$ (μM) |
| --- | --- |
| 5-Fluorouracil | 60 |
| 2'-Deoxy-5-(1-fluoroethenyl)-uridine | 9.4 |
| 2'-Deoxy-5-(1-fluoroethenyl)-uridine in combination with 5-Fluorouracil | 0.70 |

What is claimed is:

1. A compound of the formula:

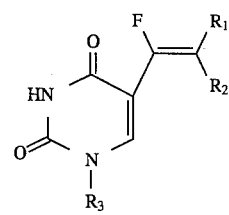

wherein $R_1$ and $R_2$ are each independently hydrogen, $C_1$–$C_4$ alkyl, or a phenyl group unsubstituted or substituted with from 1 to 3 substituents, wherein each substituent is selected from the group consisting of $C_1$–$C_4$ alkyl and $C_1$–$C_4$ alkoxy; and $R_3$ is hydrogen, ribose, 2'-deoxyribose or arabinose.

2. A compound according to claim 1 wherein $R_3$ is 2'-deoxyribose.

3. A compound according to claim 1 wherein $R_1$ and $R_2$ are hydrogen.

4. A compound of claim 1 wherein the compound is 2'-deoxy- 5-(1-fluoroethenyl)uridine.

5. A compound of claim 1 wherein the compound is 5-(1-fluoro- 2,2-dimethyl-ethenyl)uridine.

6. A compound of claim 1 wherein the compound is (E)-5-(1-fluoro-2-phenyl-ethenyl)uridine.

7. A compound of claim 1 wherein the compound is (E)-2'-deoxy-5-(1-fluoro-2-phenyl-ethenyl)uridine.

8. A compound of claim 1 wherein the compound is 5-(1-fluoroethenyl)uracil.

* * * * *